(12) United States Patent
Ceppaluni et al.

(10) Patent No.: US 6,722,529 B2
(45) Date of Patent: Apr. 20, 2004

(54) AIR FLOW SCENT ENHANCER

(76) Inventors: Michael J. Ceppaluni, 284 Cassville Rd., Jackson, NJ (US) 08527; Thomas E. Plunkett, 228 Crescent Ave., Jackson, NJ (US) 08527

( * ) Notice: Subject to any disclaimer, the term of this patent is extended or adjusted under 35 U.S.C. 154(b) by 88 days.

(21) Appl. No.: 10/121,599

(22) Filed: Apr. 15, 2002

(65) Prior Publication Data

US 2003/0192922 A1 Oct. 16, 2003

(51) Int. Cl.[7] .................................................. B67D 5/08
(52) U.S. Cl. ......................... 222/63; 222/648; 222/649
(58) Field of Search .................. 222/63, 642, 645–649, 222/402.1; 422/124

(56) References Cited

U.S. PATENT DOCUMENTS

| | | | | |
|---|---|---|---|---|
| 5,924,597 | A | * | 7/1999 | Lynn .............................. 222/1 |
| 6,267,297 | B1 | * | 7/2001 | Contadini et al. ............. 239/1 |
| 6,379,242 | B1 | * | 4/2002 | Wiseman, Sr. et al. ..... 454/337 |
| 6,419,122 | B1 | * | 7/2002 | Chown ........................ 222/162 |

* cited by examiner

*Primary Examiner*—Joseph A. Kaufman
(74) *Attorney, Agent, or Firm*—Charles I. Brodsky

(57) ABSTRACT

A housing mounted to the ductwork of a hot air heating system or a central air conditioning system includes a pressure differential switch to sense the forced air flow in actuating a spray dispenser to discharge a freshening, deodorizing and/or disinfecting spray through a nozzle and provided hose into the ductwork, for a duration and at a repetition rate predetermined in accordance with the cleansing results desired.

7 Claims, 6 Drawing Sheets

6,722,529 B2

AIR FLOW SCENT ENHANCER

CROSS-REFERENCE TO RELATED APPLICATIONS NONE

STATEMENT REGARDING FEDERALLY SPONSORED RESEARCH OR DEVELOPMENT

Research and development of this invention and Application have not been federally sponsored, and no rights are given under any Federal program.

REFERENCE TO A MICROFICHE APPENDIX NOT APPLICABLE

BACKGROUND OF THE INVENTION

1. Field of the Invention

This invention relates to an air flow scent enhancer apparatus and system, in general, and to such apparatus as is usable in combination with the ductwork of a hot air heating system or a central air conditioning system in a home or office, in particular.

2. Description of the Related Art

The benefits of battery operated air fresheners in public restroom use have been known for some time. However, its applicability in home or office use is not only generally impractical, but to incorporate such air fresheners in every room is cost prohibitive at best. Still, having an ability to introduce a pleasant scent throughout the home or office to mask odors or otherwise would be a desirable thing to have especially if the cost to do so were kept down and reasonably low. Those continuously operating plug-in air freshening units powered from a wall outlet suffer the disadvantages that once activated, the gels employed are used up within a 30 days period, while their expense militates against their use in every room of the home or office. Several of these plug-in manufactures, furthermore, become even more undesirable, in their having to be replaced entirely, rather than just replacing the scent air freshener, deodorizer or disinfectant employed.

SUMMARY OF THE INVENTION

As will become clear from the following description, the air flow scent enhancing apparatus of the present invention proceeds upon the recognition that there exists in just about every home and/or office complex, a hot air heating system or a central air conditioning system connectable by various ductwork. Recognizing further that the blowers in such systems periodically go "on" and "off", the present invention proceeds to utilize the forced air that flows when "on" to, itself, actuate a spray dispenser of air freshener, deodorizer or disinfectant to discharge its spray into the ductwork so as to be carried along into every room of the home or office by the forced air then flowing. As will become clear from the following description, a pressure differential switch is employed to sense the presence of such forced air flow in actuating an electrical circuit and connected motor in a preferred embodiment, to control a cam in actuating, for example, the pressure cap of an aerosol can spray, whose discharge nozzle is then connected by a hose which extends into the system ductwork. In accordance with the invention, the electrical circuit can be designed by those skilled in the art to dispense the air freshening, deodorizing or disinfectant spray a predetermined time interval (as 1, 2 or 3 seconds), at a repetition rate or frequency of every 15, 20 or 25 minutes, for example—in any instance, only for so long a period of time as the blower continues to force along the air flow.

In a preferred embodiment of the invention, the air flow scent enhancing apparatus includes a housing with a removable cover in providing access to insert the aerosol can or other spray dispenser, and to replace it when emptied. The housing may likewise incorporate one or more adapters to mount or connect with a side of the ductwork found, along with an outlet to extend the hose at one end to a discharge nozzle of the dispenser—and at an opposite end, through a hole made in the ductwork so as to introduce the spray to be carried about by the forced air flow. By so doing, the apparatus of the invention will be seen to additionally provide a manner by which dust and/or bacteria buildup within the ductwork can similarly be cleaned and blown away—all in an arrangement that can be installed simply and easily in a matter of just a few minutes, as by providing a mounting hole(s) on the ductwork, and by providing an input port adjacent the housing to receive the hose coupling. With the pressure differential switch also extending into the ductwork through yet a further opening made by the user, once the forced air flow is sensed, the electric circuit is actuated to generate the air freshening, deodorizing or disinfecting spray for the time interval selected, and to be repeated at regular intervals while the blower continues to operate. Just to replenish the scent at a later date, even when the heating or air conditioning system is not "on", the homeowner or office worker can simply turn on a "fan" switch at the controlling thermostat—and, in this manner generate a forced air flow which is detected by the pressure differential switch sensor within the confines of the duct.

BRIEF DESCRIPTION OF THE DRAWINGS

These and other features of the present invention will be more clearly understood from a consideration of the following description, taken in connection with the accompanying drawings, in which.

DETAILED DESCRIPTION OF THE INVENTION

Figure 1:
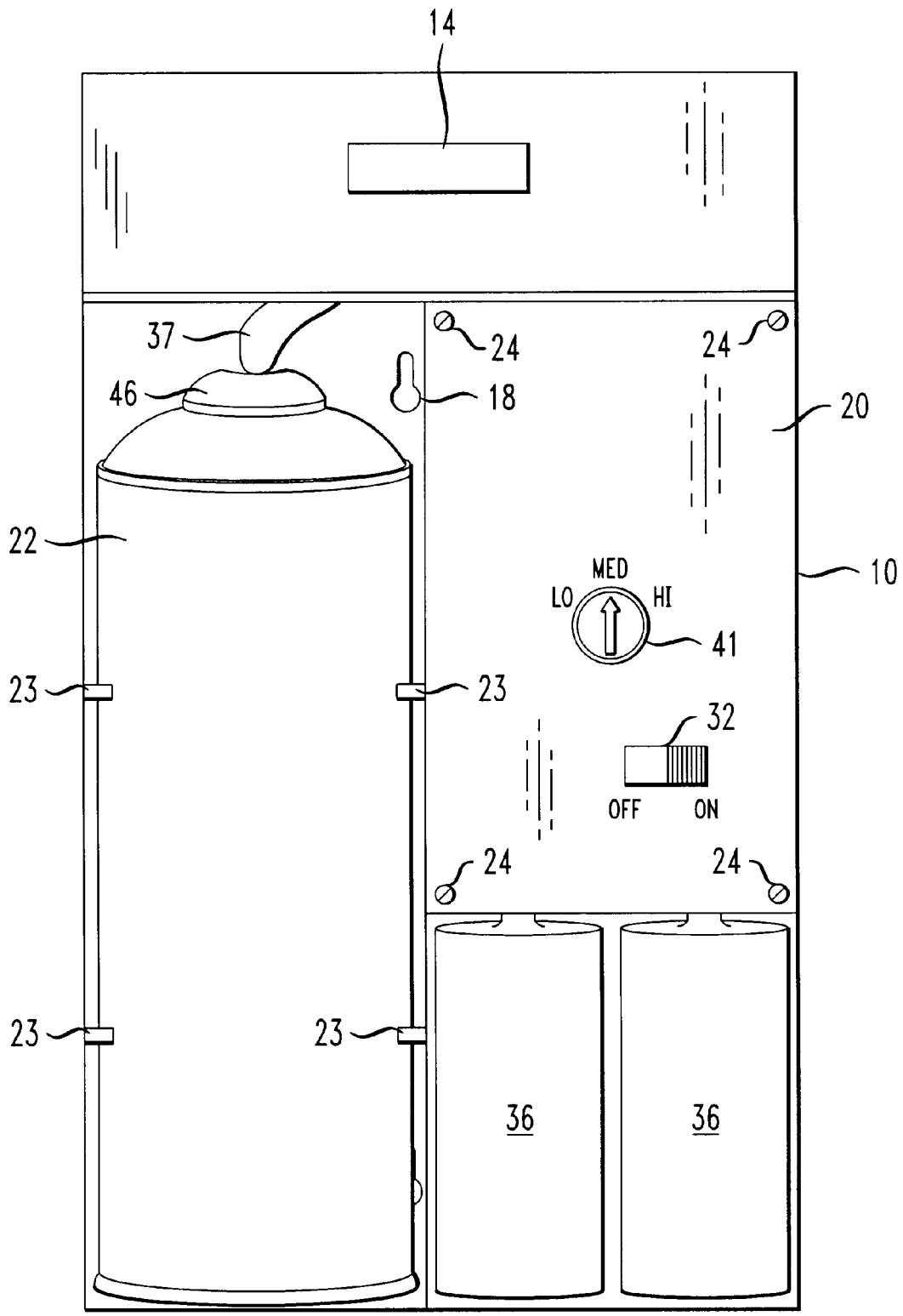
FIGS. 1–3 are schematic views of a preferred housing of the invention, with its cover removed, helpful in an understanding of its construction.
Figure 2:
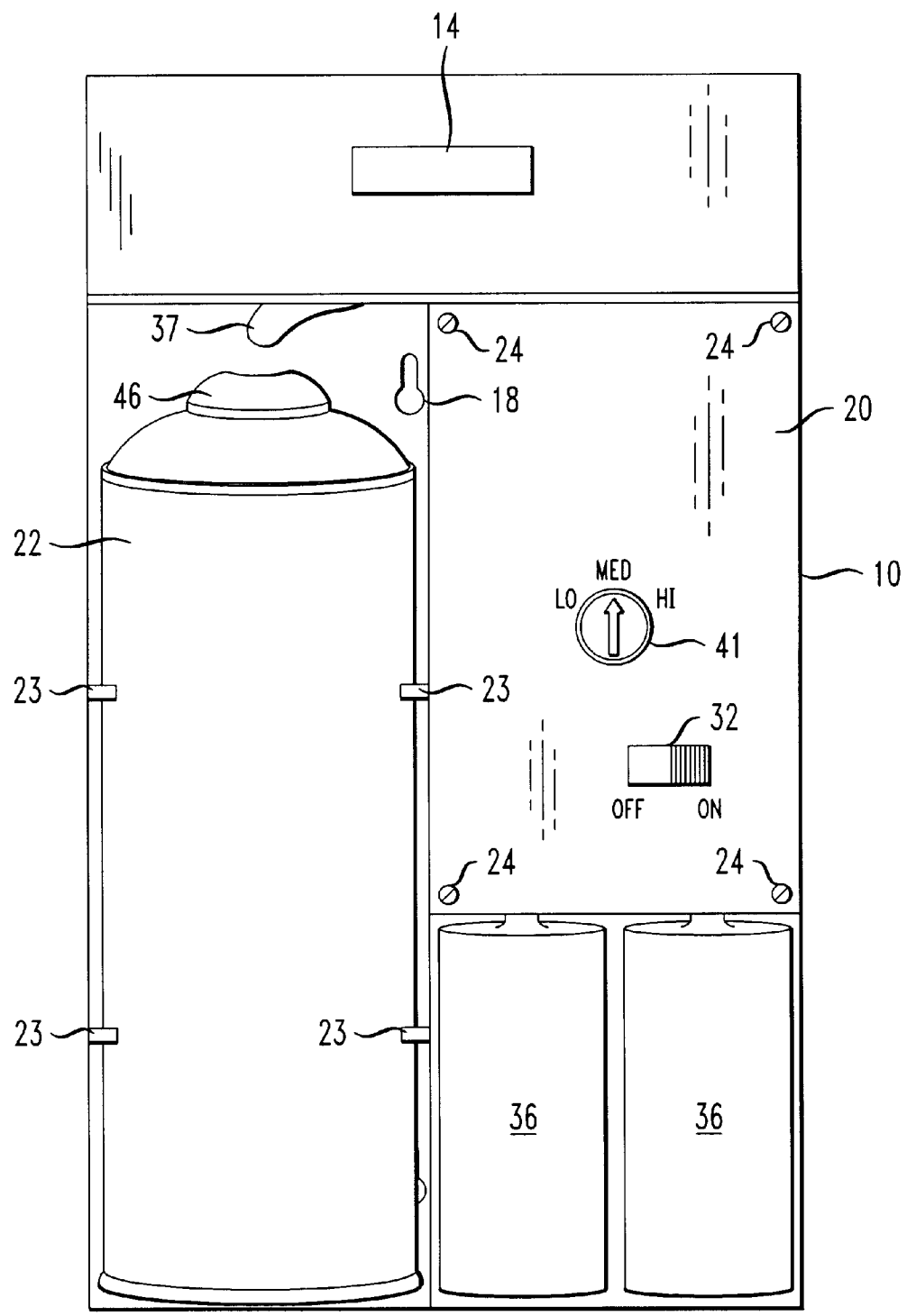

In the Drawings, the housing 10, with a front cover 12 and with a manufacturer's nameplate 14, is mountable on a side of the ductwork 15 of a hot air heating system or central air conditioning system in a home or office complex (not shown) by one or more self tapping screws 16 through mounting apertures in the rear of the housing, as at 18. Removing the front cover 12 reveals the configuration of FIGS. 1 and 2, while removing its service cover 20 provides the presentation of FIG. 3 with the spray dispenser set aside. Such dispenser 22, as shown in FIGS. 1 and 2, is secured in place by a series of clips 23 which enable the dispenser 22 to be releasably snapped in place. A further series of screws, emplaced at 24, fix the service cover 20 in position.

Figure 3:
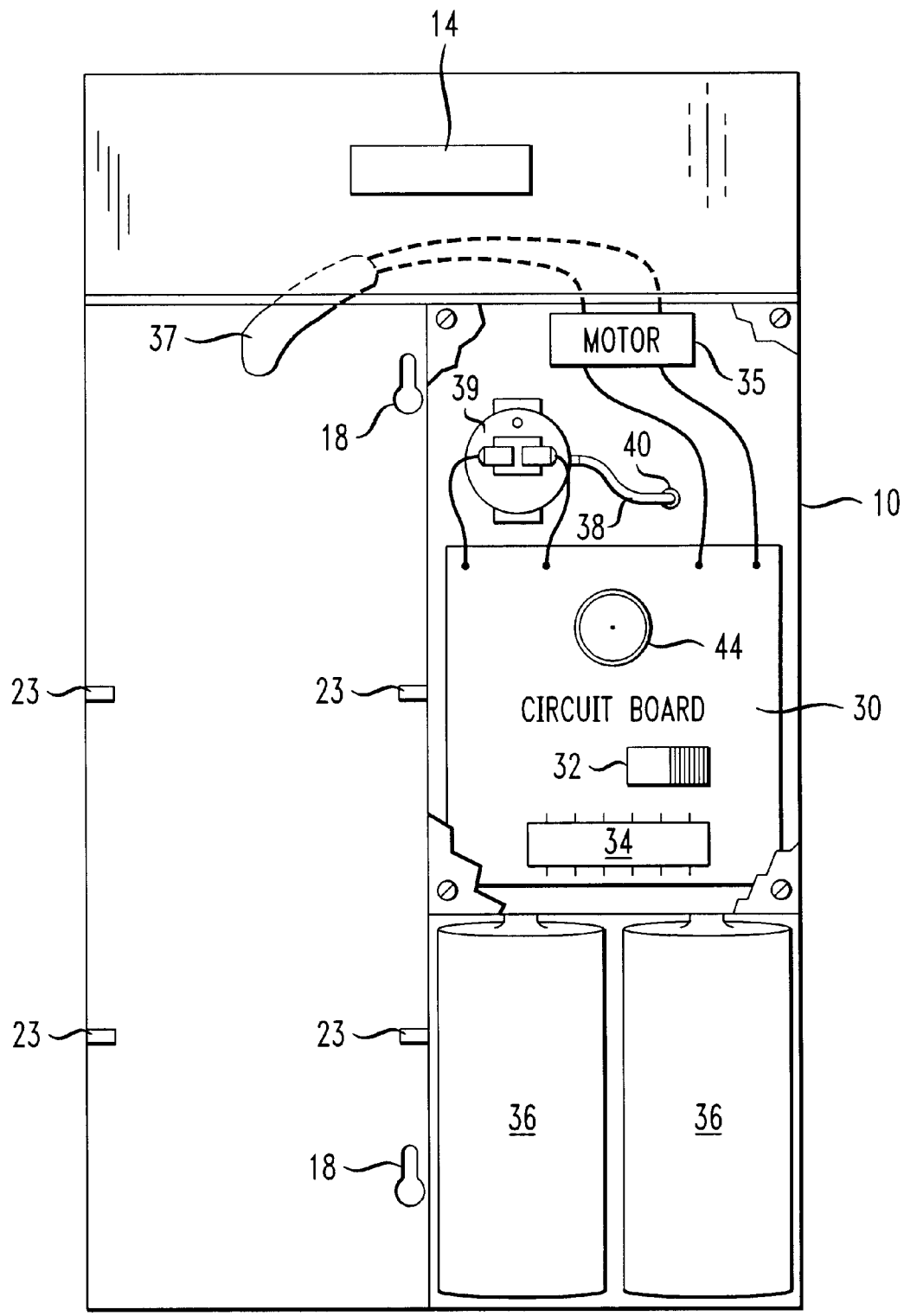

As shown in FIG. 3, the housing 10 includes an electric circuit board 30 having its own "on-off" switch 32. The components of the circuitry are shown at 34, and are powered by a battery source, generally shown at 36. Such circuit board 30 couples in turn to an internal motor 35 for driving a cam 37. Coupled with the circuit board 30 is a pressure differential switch 39, having an appropriate sensing tube 38 which extends from within the housing 10 through an aperture 40 into the ductwork 15 by means of a hole 42 cut into the ductwork by the homeowner or office worker. If desired, a selector control 41 is also provided within the service compartment 25 to allow a user to vary the timing of the operation of the electric circuit board 30 in well known manner to vary the duration of a resultant spray of, for example, 1, 2, or 3 seconds—depending upon whether the spray to be injected is to be of a "low", "medium", or "high" strength effect.

Figure 4:
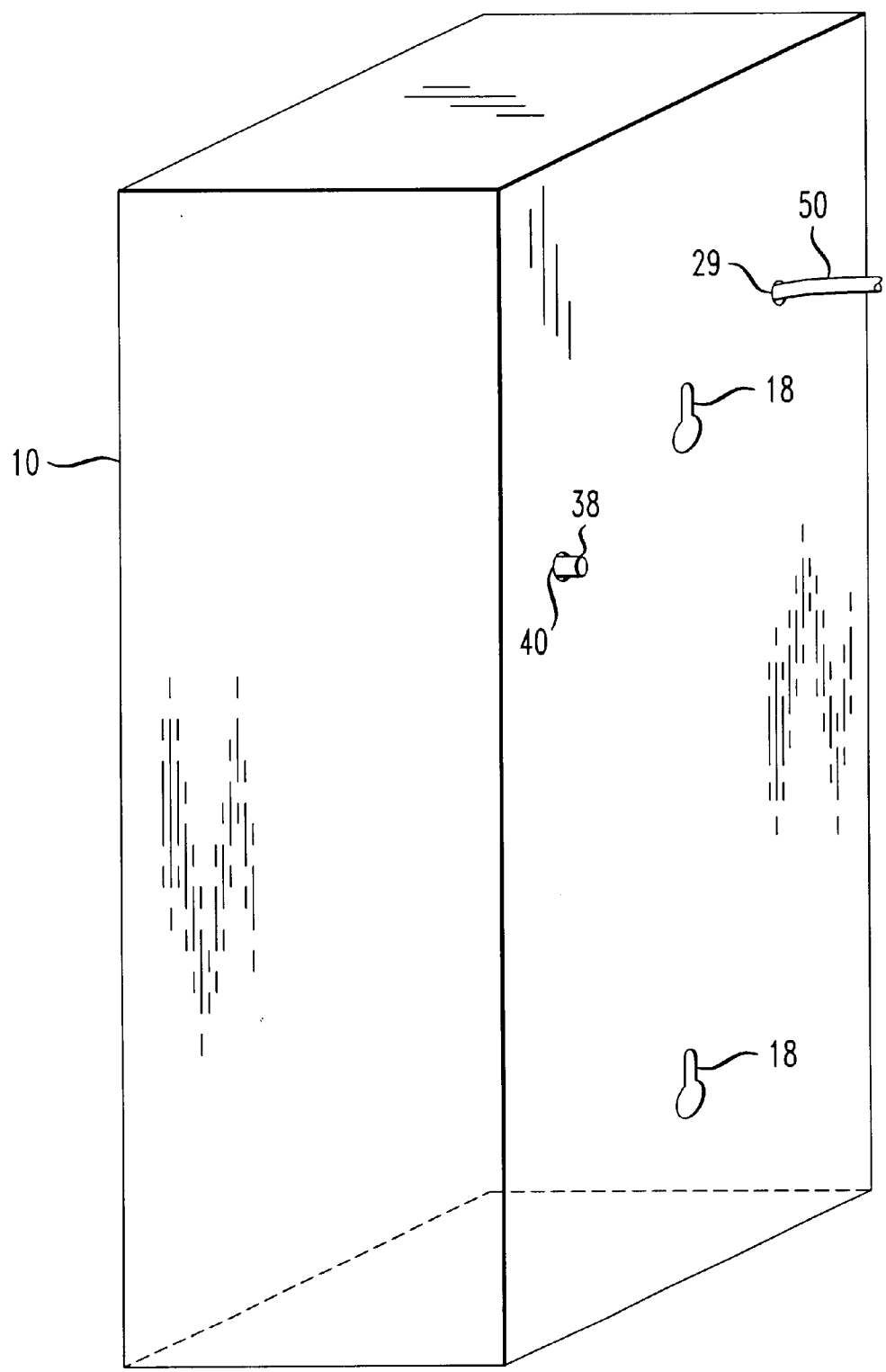
FIGS. 4–5 are pictorial views helpful in an understanding of the housing unit of FIGS. 1–3 as it would be employed with the ductwork of a hot air heating system or central air conditioning system of a home or office complex.
Figure 5:
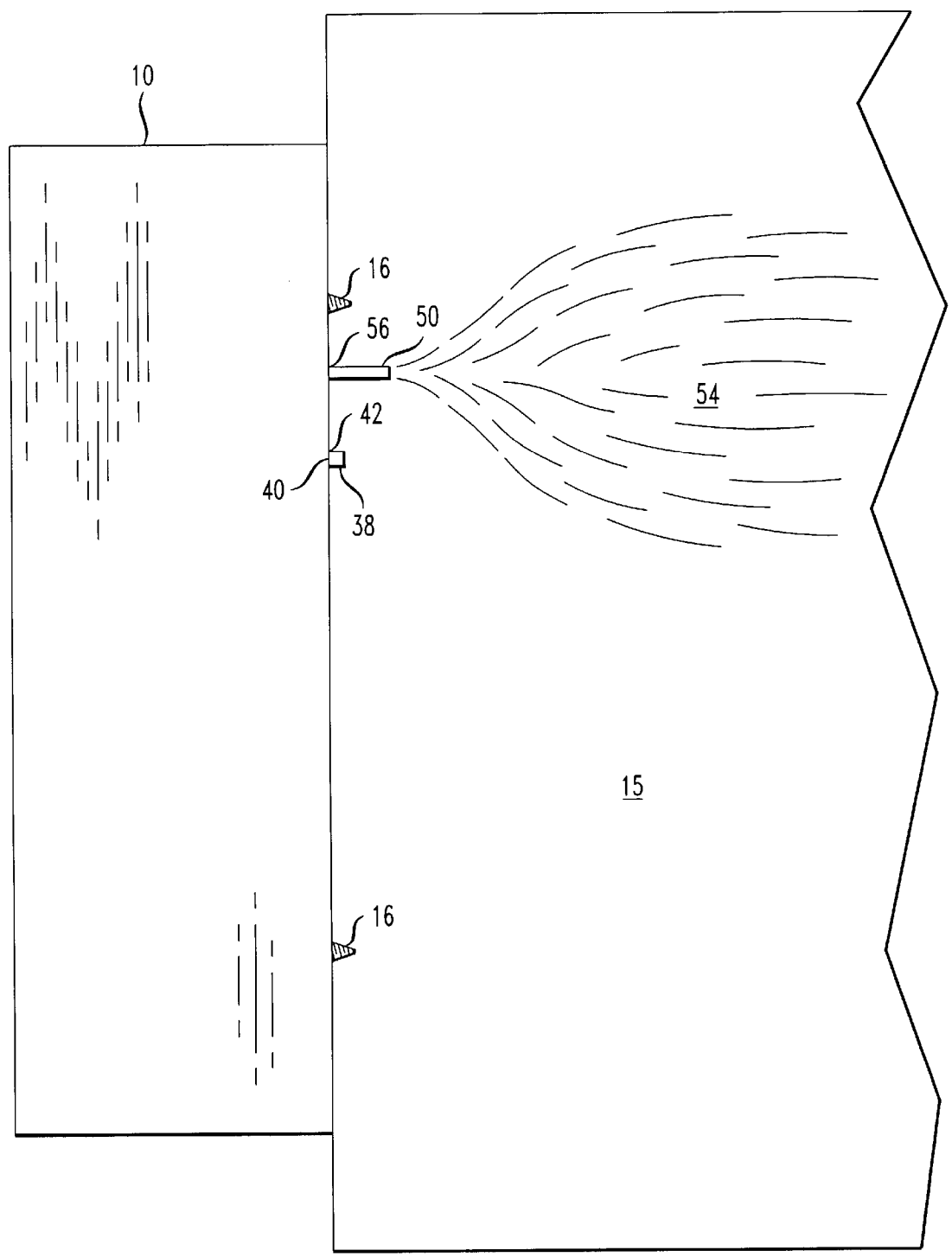
Figure 6:
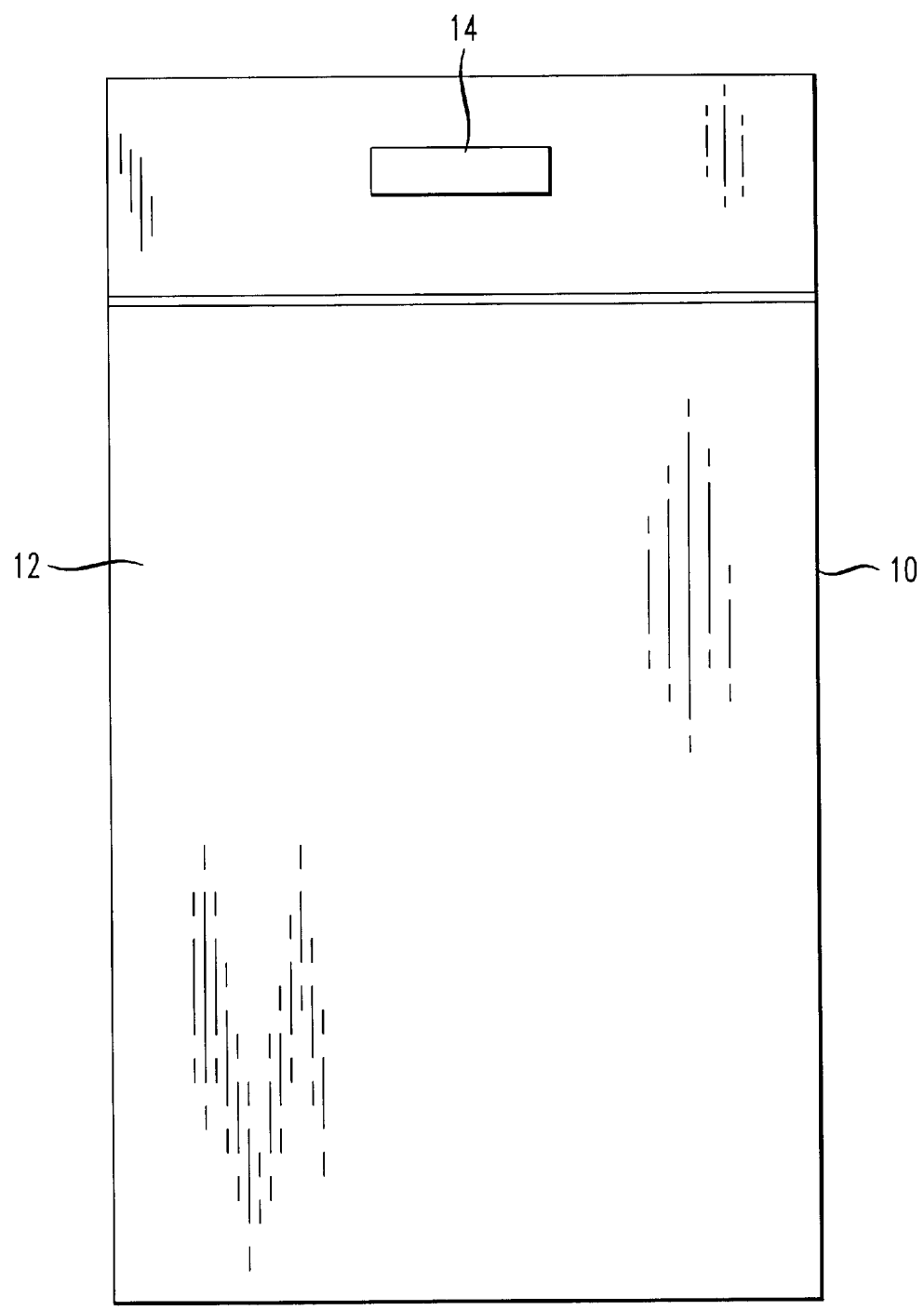
FIG. 6 is a front view of the housing of the invention with its cover in place.

Such spray is produced by the dispenser 22—which may be of any available type, such as an aerosol can. As illustrated, in FIG. 2, with the switch 32 in its "OFF" position, the electric circuit board 30 co-acts with the internal motor 35 to retract the actuator cam 37 away from the pressure control 46 of the dispenser in producing no effective spray. On the other hand, as shown in FIG. 1, with the sensing tube 38 of the pressure differential switch 39 detecting a blower flow of forced-air in the ductwork 15, and with the switch 32 in its "ON" position, the electric circuit board 30 and motor 35 operate in a direction to force the actuator cam 37 against the pressure control 46, in discharging its spray. However in securing the dispenser 22 in position between its securing clips 23, its orientation is such that the discharge nozzle of the dispenser 22 extends rearwardly towards an aperture 29 of the housing 10 (as in FIGS. 4 and 5) to join with a hose 50 coupling the nozzle through the housing 10 and into the ductwork 15. Such hose 50 thereby sprays a misted product 54 (in the nature of an air freshener, a deodorizer, or a disinfectant, for example) into the ductwork 15, to be carried along into the various rooms of the home or office complex served by the ductwork 15, as the blower continues to operate. This second ductwork aperture 56 is likewise cut into the ductwork 15 by the user which, together with the cutting of the aperture 42 and the insertion of the self-tapping screw(s) 16, should take no more than a matter of a few minutes.

As will be appreciated, appropriate design of the electric circuit board 30—with, or without the user provided adjustment via the selector control 41—allows setting a repetition rate as to when the spray operation by the actuator cam 37 repeats in establishing recurring sprays at 15, 20, 25, etc. minute intervals, as desired. On the other hand, once a forced air flow detected by the pressure differential switch 39 ends, an interruption occurs in the electric circuit board operation to deactivate the motor 35 and the actuator cam 37 in disconnecting any spray that may be ongoing, and in preventing a recurrent spray until the pressure differential switch 39 once again recognizes the presence of the blower induced forced air flow.

In such manner, a single spray dispenser is utilizable in freshening, deodorizing and/or disinfecting the air in each room of the home or office complex, substantially simultaneously. Not only is just one dispenser required, but only one needs to be replaced when empty. Because the operation can be turned "on" or "off" by the switch control 32, the scent dispensing is provided only at a time desired by the user, instead of "continuously" with those types of plug-in units presently being marketed for individual room control. And, of equal importance, the length of the dispensing spray, along with its repetition rate, are controllable timewise, to be effective only when the blower is operating during the heating or air conditioning cycle, or when it is just desired to "freshen" the home or office by turning "on" the system fan.

While there have been described what are considered to be preferred embodiments of the present invention, it will be readily appreciated that modifications can be made by those skilled in the art without departing from the teachings herein. For example, whereas the present invention has been described in the context of one where the dispensing spray insertion into the ductwork automatically ceases once the blower shuts off, the electric circuitry of the board 30 can be designed to allow a measured time delay of operation even after the pressure differential switch 39 senses the cut off of forced air flow. The air flow scent enhancing apparatus will continue to operate in providing its advantages over the prior art constructions and, for at least such reason, resort should be had to the claims appended hereto for a true understanding of the invention.

We claim:

1. An air flow scent enhancing apparatus comprising:
   a housing;
   first means for mounting said housing to a ductwork of a hot air heating system or a central air conditioning system;
   a hose extending from within said housing to an outside thereof;
   second means for accepting a dispenser of one of an air freshener, deodorizer and disinfectant spray having a discharge nozzle;
   third means including a battery powered electrical circuit for actuating an accepted dispenser to operate in discharging said air freshener, deodorizer disinfectant spray;
   and a pressure differential switch coupled to said third means and extending through said housing for controlling said third means to actuation only in response to a detected flow of forced air.

2. The combination of claim 1 wherein said dispenser is releasably securable within said housing for replacement when empty.

3. The combination of claim 1 wherein a discharge outlet of said dispenser includes a spray nozzle, and wherein said third means includes said hose coupling said nozzle through said housing into said ductwork.

4. The combination of claim 3 wherein said dispenser is mechanically actuable to discharge said air freshener, deodorizer or disinfectant spray, and wherein said third means includes a cam operable to actuate said dispenser in response to said detected presence of forced air flow within said system ductwork.

5. The combination of claim 4 wherein said third means additionally include said battery powered electrical circuit controlling said cam to operation in the presence of said detected forced air flow.

6. The combination of claim 5 wherein said third means further includes a motor in actuating said cam into operation in the presence of said detected forced air flow.

7. The apparatus of claim 1 wherein said second means is capable of accepting an aerosol can spray dispenser.

\* \* \* \* \*